US006521257B1

(12) United States Patent
Taniguchi et al.

(10) Patent No.: US 6,521,257 B1
(45) Date of Patent: Feb. 18, 2003

(54) GELLED COMPOSITIONS

(75) Inventors: Shigeru Taniguchi, Kanagawa (JP);
Tomonori Yonezu, Kanagawa (JP);
Hitomi Izumi, Kyoto (JP); Yoshihiro Hishikawa, Kanagawa (JP)

(73) Assignee: Ohkura Pharmaceutical Co., Ltd., Kyoto (JP)

( * ) Notice: Subject to any disclaimer, the term of this patent is extended or adjusted under 35 U.S.C. 154(b) by 0 days.

(21) Appl. No.: 09/446,600

(22) PCT Filed: Jun. 19, 1998

(86) PCT No.: PCT/JP98/02741

§ 371 (c)(1),
(2), (4) Date: Mar. 6, 2000

(87) PCT Pub. No.: WO98/58654

PCT Pub. Date: Dec. 30, 1998

(30) Foreign Application Priority Data

Jun. 20, 1997 (JP) .............................. 9-164816

(51) Int. Cl.[7] .......................... A61K 9/14; A61K 9/68; A61K 31/74; A61F 13/00
(52) U.S. Cl. ...................... 424/484; 424/440; 424/434; 424/78.1
(58) Field of Search .................. 424/78, 440, 78.1, 424/434, 484

(56) References Cited

U.S. PATENT DOCUMENTS

| 3,974,272 | A | * | 8/1976 | Polli et al. ..................... 424/78 |
| 4,857,331 | A | | 8/1989 | Shaw et al. |
| 4,882,153 | A | * | 11/1989 | Yang et al. .................. 424/440 |
| 5,102,664 | A | * | 4/1992 | Day ........................... 424/439 |
| 5,464,612 | A | * | 11/1995 | Matoba et al. .............. 424/78.1 |
| 5,578,217 | A | * | 11/1996 | Unger et al. ................. 210/670 |
| 5,942,242 | A | * | 8/1999 | Mizushima et al. ......... 424/434 |

FOREIGN PATENT DOCUMENTS

| EP | 0190826 | 8/1986 |
| EP | 0366255 | 5/1990 |
| JP | 63-230.636 | 9/1988 |
| JP | 2-62831 | 2/1990 |

OTHER PUBLICATIONS

Oakenfull et al., "Gelation Mechanisms," *Foods Food Ingredients J. Jpn.* No. 167, pp. 48–68 (1996).
Whistler et al., *Industrial Gums: polysaccharides and their derivatives*, 3rd ed., Chapters 5, 6 and 7, Academic Press, San Diego, CA (1993).
Toyoguchi, T. et al.: Jpn. IYAKU NO MON, 31: 50–55, 1991.
Norioka, T. et al.: *Jpn. Medical Consultation & New Remedies*, 29: 208–214, 1992.
Sato, Y. et al.: *Jpn. Basic Pharmacology & Therapeutics*, 21: 379–386, 1993.
Sasaki, Y. et al.: *Jpn. Medical Consultation & New Remedies*, 31: 73–76, 1994.
Hanawa, T. et al.: *Jpn J. Hosp. Pharm.*, 22: 433–443, 1996.
Toraishi, K. et al.: *Jpn. J. Hosp. Pharm.*, 24: 479–483, 1998.

* cited by examiner

*Primary Examiner*—Thurman K. Page
*Assistant Examiner*—Blessing Fubara
(74) *Attorney, Agent, or Firm*—Klarquist Sparkman, LLP

(57) ABSTRACT

A gelled composition was provided by adding a gelling component to a carrier for adsorption. Not only was the taste of the carrier for adsorption significantly reduced in this composition, but the dosage was also decreased so that the composition could be easily taken by a patient.

52 Claims, No Drawings

GELLED COMPOSITIONS

TECHNICAL FIELD

The present invention relates to a gelled composition for internal use. It comprises a carrier for adsorption as an effective ingredient, and belongs to the fields of medicine and food.

BACKGROUND ART

Most conventional medicines comprising a carrier for adsorption as an effective ingredient generally require large dosages and are orally administered after being suspended in water or the like medium. However, the compliance from patients has been extremely low for several reasons. First, it is necessary to suspend the carrier for adsorption in water prior to administration, and this procedure is tedious. Second, the carrier for adsorption leaves a strong taste in the mouth. Third, the patient may sense a foreign substance in the mouth due to the remaining carrier. Fourth, it has been very difficult to take an effective dosage for treatment because of the relatively large dosage of the carrier for adsorption as compared with other preparations. Finally, the unpleasant feeling of a foreign substance in the mouth while taking such a composition often caused side effects such as nausea or vomiturition. There has thus been a problem in medical treatment since the desired treatment effect of the medicine cannot be fully obtained even though its high usefulness has been clinically established.

DISCLOSURE OF THE INVENTION

An objective of this invention is to provide an easily taken composition comprising a carrier for adsorption as an effective ingredient.

Conventional pharmaceutical preparations that include a carrier for adsorption as an effective ingredient must be suspended in water or the like medium before being taken. Furthermore, the carrier for adsorption often has a strong taste and requires a large dosage. Together, these caused a significant reduction in patients' compliance with taking the preparation. Conventional pharmaceutical preparations also pose a serious problem in that simply decreasing the amount of solvent used for the carrier for adsorption increased the unpleasant taste of that carrier, resulting in further reduction of patients' compliance (no improvement of patients' compliance at all). The present inventors focused their attention on these issues.

The present inventors considered that the unpleasant taste was caused by the difference in the taste between the carrier for adsorption and the medium such as water. We therefore sought a dosage composition that would taste less like the carrier for adsorption. Subsequently, we succeeded in not only significantly decreasing the dosage but also reducing the taste of the carrier for adsorption by adding a gelling component to a composition comprising the carrier for absorption, thus providing a gelled composition. Furthermore, the present inventors found it possible to apply the gelled composition thus prepared not only to medicines but also to foods such as health foods.

The present invention thus relates to a composition that has less of the taste of the carrier for adsorption that is comprised as an effective ingredient. The present invention also relates to its application for medicine and food. More specifically, the present invention relates to:

(1) a gelled composition for internal use comprising a carrier for adsorption as an effective ingredient, (2) the gelled composition according to (1), wherein said carrier for adsorption is an ion exchange resin, (3) the gelled composition according to (2), wherein said carrier for adsorption is selected from the group consisting of cholestyramine, calcium polystyrene sulfonate, or sodium polystyrene sulfonate, (4) the gelled composition according to (1) wherein the composition comprises pectin as a gelling agent, (5) the gelled composition according to (1) wherein the composition comprises pectin and agar as the gelling agent, (6) a pharmaceutical preparation comprising the gelled composition for the internal use according to any one of (1) to (5), and (7) a food comprising the gelled composition for internal use according to any one of (1) to (5).

Herein, "gelled" refers to highly viscous liquid, semiliquid, semisolid or solid states.

A gelled composition of this invention comprises a carrier for adsorption and a gelling agent as the effective ingredients. There is no particular limitation on the type of carriers for adsorption as long as they are water-insoluble. For example, anion-exchange resin, cation-exchange resin, or activated carbon granules for adsorption can be used.

An anion-exchange resin such as cholestyramine and a cation-exchange resin such as calcium polystyrene sulfonate or sodium polystyrene sulfonate can be employed in the present invention as the specific agent in the carrier for adsorption. Furthermore, the type of gelling agent is not particularly limited. For example, pectin, agar, arabic gum, xanthum gum, tragacanth gum, karaya gum, ghatti gum, guar gum, gellan gum, locust bean gum, alginic acid or its salt (e.g., sodiumalginate), carrageenan, gelatin, dextrin, starches (corn starch, rice starch, wheat starch, potato starch, pueraria starch, tapioca starch, carboxymethyl starch, hydroxypropyl starch, hydroxyethyl starch, chemically cross-linked starch, α-starch, and so on), celluloses (hydroxypropylmethyl cellulose, carboxymethyl cellulose, methyl cellulose, methylethyl cellulose, hydroxypropyl cellulose, crystalline cellulose and so on), polyvinyl alcohol, polyvinylpyrrolidone, polyethylene glycol (macrogol), or mannans can be used singly or in an appropriate combination. Of these, a complex gel comprising pectin and agar is especially preferable because this complex gel is able to significantly reduce the peculiar taste of a carrier for adsorption.

The content of a carrier for adsorption in the gelled composition according to this invention varies depending on the amount of effective ingredient of the pharmaceutical preparation, or the swelling rate (water absorption rate) of the carrier for adsorption. However, it usually ranges from 0.1% to 50.0% (w/w %, same hereafter) relative to the total amount of the pharmaceutical preparation, and preferably from 5.0% to 20.0% for cholestyramine, and 10.0% to 30.0% for calcium polystyrene sulfonate or sodium polystyrenesulfonate. The gelling agent content usually ranges from 0.01% to 10.0%, and preferably 0.5% to 2.5% for pectin, 0.1% to 0.5% for agar, and 0.5% to 2.0% for gelatin.

A gelled composition of this invention may further contain, as needed, a stabilizer, surfactant, solubilizer, buffer, sweetener, seasoning, suspending agent, coating, flavor/spice (aromatic), colorant, pH adjuster, viscosity increasing agent, Ca-supplier, dispersant, antiseptic (preservative), solvent (dissolving agent) and the like. For example, sodium alginate, various gums, glycerin, etc. can be used as a stabilizer; sodium lauryl sulfate, polysorbate 80, or the like can be used as a surfactant; ethanol or the like can be used as a solubilizer; phosphate, carbonate, and so on can be used as a buffer; purified sucrose, aspartame, fructose, sorbitol, xylitol, glucose, mannitol, maltose, trehalose, palatinose, powdered-reduced maltose millet jelly, oligosaccharide, erythritol, stevioside, glycyrrhizin, etc. can be used as a sweetener; menthol, edible fruit juice, caramel, or glucono-(-lactone, etc. can be used as a seasoning; sodium alginate, arabic gum, lactose, or the like can be used as a suspending agent; purified shellac, hydroxypropylmethyl cellulose phthalate, or the like can be used as a coating; fruit flavor, prune, mint oil, and so on can be used as a flavor/spice (aromatic); orange essence, edible dye, caramel, or the like can be used as a colorant; citric acid or its salt, tartaric acid or its salt, succinic acid, lactic acid, calcium lactate, phosphate, glucono-$\delta$-lactone, etc. can be used as a pH adjuster; dextrin, xanthum gum, soybean lecithin, polyethylene glycol, etc. can be used as a viscosity increasing agent; calcium lactate, calcium hydrogenphosphate, calcium carbonate, calcium chloride, calcium citrate, calcium sulfate, etc. can be used as a Ca-supplier; arabic gum, starches, crystalline cellulose, lactose, etc. can be used as a dispersant; sorbic acid or its salt, benzoic acid or its salt, p-oxybenzoates, or the like can be used as an antiseptic (preservative); and purified water or ethanol, or the like can be used as a solvent (dissolving agent).

To prepare a gelled composition of this invention, a gelling agent is added to water or the like medium and completely dissolved, for example, by heating. This solution is then heated, and a carrier for adsorption is gradually added thereto to make it homogeneous. To this mixture are added a sweetener and other additives required for gelation. The resulting mixture is blended until it becomes homogeneous. The proper amounts of the mixture are then poured into appropriate containers (aluminum stick cases or cup containers) (if necessary, treatments such as aseptic filling or retort sterilization can also be performed). The containers are then preferably cooled to room temperature or below for 30 min to 5 h to gel the mixture. The gelled composition of this invention thus prepared may be taken as such.

BEST MODE FOR IMPLEMENTING THE INVENTION

The following describes the present invention in more detail with reference to examples, but the present invention should not be construed to be limited by these examples.

EXAMPLE 1

A gelled composition containing cholestyramine was prepared using the components in the blended amounts described in Table 1. In particular, pectin, as the gelling agent, was dissolved in purified water at room temperature, heated to about 85° C., and blended with the carrier for adsorption and other additives. After the mixture was thoroughly stirred to homogeneity, predetermined single dosages were distributed into containers (aluminum stick cases or cup containers), sealed, and cooled at room temperature to obtain the pharmaceutical preparation according to this invention. The pharmaceutical preparation thus obtained was a viscous, relatively sour tasting semisolid. The rough taste peculiar to the carrier for adsorption was reduced in this preparation, and there was less feeling of a foreign substance in the mouth.

TABLE 1

| Component | Blended amount (g) |
| --- | --- |
| Cholestyramine | 5.000 |
| Pectin | 0.600 |
| Potassium sorbate | 0.030 |
| Calcium lactate | 0.030 |
| Citric acid | 0.200 |
| Purified sucrose | 2.500 |
| Purified water | 21.640 |
| Total amount | 30.000 g |

EXAMPLE 2

A gelled composition was prepared using the components described in Table 2 by the method indicated below. In particular, purified water was divided in two equal portions. Pectin was dissolved in one portion, which was then heated to about 85° C. Gelatin was allowed to swell with the other portion of purified water at room temperature, dissolved by heating, and mixed with the previously prepared pectin solution. The gelled composition was then prepared according to Example 1. However, in this case, the composition was allowed to stand at low temperature (about 4° C.) for 2 h or more after being poured into containers, then cooled in order to solidify it and obtain the pharmaceutical preparation of this invention. The preparation thus obtained was solid and had high shape-retaining ability. The preparation was less sticky in the mouth and became easier to swallow because it had less viscosity than the composition in Example 1.

TABLE 2

| Component | Blended amount (g) |
| --- | --- |
| Cholestyramine | 5.000 |
| Pectin | 0.300 |
| Gelatin | 0.300 |
| Calcium lactate | 0.030 |
| Citric acid | 0.100 |
| Purified sucrose | 2.500 |
| Purified water | 21.770 |
| Total amount | 30.000 g |

EXAMPLE 3

A gelled composition was prepared using the components described in Table 3. First, pectin was dissolved in purified water at room temperature. Next, agar was added to this solution, which was heated to about 90° C. and then stirred until the agar was completely dissolved. Next, the same procedures as in Example 1 were performed to obtain the pharmaceutical preparation of this invention. The preparation thus obtained was solid with high shape-retaining ability similar to the composition in Example 2. An excellent preparation that is easy to take because it had appropriate elasticity and smooth taste was thus obtained. Furthermore, it was not only readily soluble in the mouth but also left almost no feeling of incongruity derived from the carrier for adsorption after it was taken.

TABLE 3

| Component | Blended amount (g) |
| --- | --- |
| Cholestyramine | 4.000 |
| Pectin | 0.350 |
| Agar | 0.120 |
| Citric acid | 0.120 |
| Purified sucrose | 5.000 |
| Purified water | 25.410 |
| Total amount | 35.000 g |

EXAMPLE 4

A gelled composition was prepared using the components described in Table 4 similarly as in Example 3 to obtain the pharmaceutical preparation of this invention. The preparation thus obtained was a solid with high shape-retaining ability like the preparations in Examples 2 and 3. An excellent pharmaceutical preparation was thus obtained, which, although slightly harder than preparations in the examples above, had a smooth taste and was so easily swallowed. Furthermore, there was no taste of the carrier for adsorption when it was taken.

TABLE 4

| Component | Blended amount (g) |
| --- | --- |
| Calcium polystyrene sulfonate | 5.000 |
| Pectin | 0.250 |
| Agar | 0.120 |
| Citric acid | 0.086 |
| Purified sucrose | 3.571 |
| Purified water | 15.973 |
| Total amount | 25.000 g |

EXAMPLE 5

A gelled composition was prepared using the components described in Table 5. In particular, pectin and a starch were dispersed, suspended in purified water, and completely dissolved by heating the suspension to about 85° C. To this solution were added the carrier for adsorption and purified sucrose; the composition was then prepared according to Example 1. The pharmaceutical preparation thus obtained was a highly viscous liquid, tasted as smooth as millet jelly, and had hardly any taste of the carrier for adsorption and, as a result, was easy to swallow.

TABLE 5

| Component | Blended amount (g) |
| --- | --- |
| Cholestyramine | 4.000 |
| Pectin | 0.700 |
| α-Starch | 0.700 |
| Citric acid | 0.050 |
| Purified sucrose | 3.500 |
| Purified water | 26.050 |
| Total amount | 35.000 g |

EXAMPLE 6

A gelled composition was prepared using the components described in Table 6 by a method similar to that in Example 5. The pharmaceutical preparation thus obtained was a semiliquid, was not as viscous as that in Example 5, and tasted relatively light.

TABLE 6

| Component | Blended amount (g) |
| --- | --- |
| Cholestyramine | 4.000 |
| Carrageenan | 0.070 |
| Locust bean gum | 0.070 |
| Purified sucrose | 5.000 |
| Purified water | 25.860 |
| Total amount | 35.000 g |

EXAMPLE 7

A gelled composition was prepared using the components described in Table 7 by a method similar to that in Example 5. Although the pharmaceutical preparation thus obtained was a semi-liquid as in Example 6, a different smoothness could be obtained by changing the additives to be used.

TABLE 7

| Component | Blended amount (g) |
| --- | --- |
| Cholestyramine | 4.000 |
| Corn starch | 0.700 |
| Dextrin | 0.700 |
| Purified sucrose | 5.000 |
| Purified water | 24.600 |
| Total amount | 35.000 g |

EXAMPLE 8

A gelled composition was prepared using the components described in Table 8. In particular, agar was dispersed in a portion of purified water and completely dissolved by heating to about 90° C. Sodium alginate and other additives were then dissolved in the remaining portion of purified water, heated to about 85° C., and mixed with the above-described agar solution. To the resulting mixture was added the carrier for adsorption. The pharmaceutical preparation thus obtained was a solid with high shape-retaining ability. It was moderately hard and could be easily crushed by the tongue. Furthermore, by replacing the sweeteners used in the above examples with sugar alcohols, it was possible to obtain a low-calorie composition with a refreshing taste.

TABLE 8

| Component | Blended amount (g) |
| --- | --- |
| Cholestyramine | 4.000 |
| Agar | 0.140 |
| Sodium alginate | 0.350 |
| Calcium hydrogenphosphate | 0.035 |
| Citric acid | 0.203 |
| Sodium citrate | 0.137 |
| Xylitol | 1.400 |
| Sorbitol | 3.600 |
| Purified water | 25.135 |
| Total amount | 35.000 g |

EXAMPLE 9

A gelled composition was prepared using the components described in Table 9 by a method similar to that in Example 8. The pharmaceutical preparation thus obtained was a solid with high shape-retaining ability similar to the preparation in Example 8. Thus, a gelled composition which was highly stable was obtained as the pharmaceutical preparation. The rough taste was significantly reduced by using agar and pectin jointly, and the water separation was restricted by the addition of carrageenan.

TABLE 9

| Component | Blended amount (g) |
|---|---|
| Cholestyramine | 4.000 |
| Pectin | 0.350 |
| Agar | 0.120 |
| Carrageenan | 0.050 |
| Potassium sorbate | 0.035 |
| Citric acid | 0.040 |
| Sodium citrate | 0.045 |
| Xylitol | 1.400 |
| Sorbitol | 3.600 |
| Purified water | 25.360 |
| Total amount | 35.000 g |

EXAMPLE 10

A gelled composition was prepared using the components described in Table 10. In particular, pectin and other additives were added to gelatin previously swelled with purified water. The mixture was then heated to about 85° C. till the components were completely dissolved in the solution. The carrier for adsorption was added to this solution, and the resulting mixture was blended to homogeneity. Cooling this solution at 4° C. for several hours yielded an excellent pharmaceutical preparation having a very elastic texture like rice cake without any rough taste at all.

TABLE 10

| Component | Blended amount (g) |
|---|---|
| Cholestyramine | 4.000 |
| Pectin | 0.350 |
| Gelatin | 0.650 |
| Xanthum gum | 0.020 |
| Citric acid | 0.050 |
| Xylitol | 1.400 |
| Sorbitol | 3.600 |
| Purified water | 24.930 |
| Total amount | 35.000 g |

EXAMPLE 11

A gelled composition was prepared using the components described in Table 11. First, agar was suspended in a predetermined portion of purified water and completely dissolved by boiling. Carrageenan and locust bean gum were dispersed in the remaining portion of purified water and dissolved by heating to about 70° C. These two solutions were combined, and the carrier for adsorption and other additives were added. The mixture was then blended to homogeneity and autoclaved for sterilization. The pharmaceutical preparation thus obtained was a solid with high shape-retaining ability, a pleasant taste without roughness, and heat-resistance to autoclaving.

TABLE 11

| Component | Blended amount (g) |
|---|---|
| Cholestyramine | 4.000 |
| Agar | 0.120 |
| Carrageenan | 0.050 |
| Locust bean gum | 0.070 |
| Sodium citrate | 0.100 |
| Xylitol | 1.400 |
| Sorbitol | 3.600 |
| Purified water | 25.660 |
| Total amount | 35.000 g |

EXAMPLE 12

A gelled composition was prepared using the components described in Table 12 by a method similar to that in Example 5. The pharmaceutical preparation thus obtained had a smooth taste derived from pectin, was low in calories due to the combined use of powdered reduced maltose millet jelly and xylitol, and was refreshingly sweet.

TABLE 12

| Component | Blended amount (g) |
|---|---|
| Calcium polystyrene sulfonate | 5.000 |
| Pectin | 0.375 |
| Dextrin | 0.250 |
| Calcium lactate | 0.050 |
| Citric acid | 0.020 |
| Powdered reduced maltose millet jelly | 2.500 |
| Xylitol | 2.500 |
| Purified water | 14.305 |
| Total amount | 25.000 g |

EXAMPLE 13

A gelled composition was prepared based on the components described in Table 13 by a method similar to that in Example 8. The pharmaceutical preparation thus obtained had a relatively elastic texture with little roughness, and was very easily taken due to the suppressed sweetness.

TABLE 13

| Component | Blended amount (g) |
|---|---|
| Calcium polystyrene sulfonate | 5.000 |
| Agar | 0.075 |
| Carrageenan | 0.050 |
| Locust bean gum | 0.050 |
| Calcium lactate | 0.050 |
| Citric acid | 0.020 |
| Powdered reduced maltose millet jelly | 2.500 |
| Aspartame | 0.015 |
| Purified water | 17.240 |
| Total amount | 25.000 g |

EXAMPLE 14

A gelled composition was prepared based on the components described in Table 14. The same additives as used in Example 9 were blended in this example. The carrier for adsorption differed from that in Example 9, but a preparation with a similarly excellent taste was obtained. It was thus inferred that an easily taken pharmaceutical preparation could be obtained without being influenced by the variety of carriers for adsorption.

TABLE 14

| Component | Blended amount (g) |
|---|---|
| Calcium polystyrene sulfonate | 5.000 |
| Pectin | 0.250 |
| Agar | 0.086 |
| Carrageenan | 0.036 |
| Citric acid | 0.029 |
| Sodium citrate | 0.032 |
| Xylitol | 1.000 |
| Sorbitol | 2.572 |
| Purified water | 15.995 |
| Total amount | 25.000 g |

EXAMPLE 15

A gelled composition was prepared using the components described in Table 15. First, agar was suspended in a predetermined portion of the purified water and completely dissolved by boiling. Next, the degradation product of reduced starch was added to the remaining portion of purified water, allowed to swell by adding gelatin, and then dissolved by heating to about 70° C. These two solutions were then combined, and the carrier for adsorption and the other components were added. The resulting mixture was blended to homogeneity to prepare the composition. The pharmaceutical preparation thus obtained was excellent in that, although its dosage was a bit large, it had a very smooth taste like soft and sweet jellied bean paste with no rough taste of the carrier for adsorption at all.

TABLE 15

| Component | Blended amount (g) |
|---|---|
| Cholestyramine | 4.000 |
| Agar | 0.500 |
| Gelatin | 1.500 |
| Degradation product of reduced starch | 1.000 |
| Xylitol | 5.000 |
| Sorbitol | 10.000 |
| Purified water | 78.000 |
| Total amount | 100.000 g |

EXAMPLE 16

A gelled composition was prepared using the components described in Table 16 according to the method in Example 15. Although the dosage was smaller in this prescription than in Example 15, the pharmaceutical preparation thus obtained had a smooth taste without any roughness of the carrier for adsorption similarly as that in Example 15. It also had excellent heat-resistance enabling it to withstand autoclave sterilization.

TABLE 16

| Component | Blended amount (g) |
|---|---|
| Cholestyramine | 4.000 |
| Agar | 0.250 |
| Gelatin | 0.750 |
| Degradation product of reduced starch | 0.500 |

TABLE 16-continued

| Component | Blended amount (g) |
|---|---|
| Xylitol | 2.500 |
| Sorbitol | 5.000 |
| Purified water | 37.000 |
| Total amount | 50.000 g |

Industrial Applicability

The present invention provides a gelled composition comprising a carrier for adsorption as an effective ingredient. The gelled composition of this invention has so little taste of the carrier for adsorption that it is extremely easy to take. Furthermore, the dosage in this gelled composition is less than that for a suspended composition in water. Therefore, when used as a medicine, this gelled composition is not only easy for a patient to take in the effective dosage but is also expected to readily improve patients' compliance in taking the preparation. Similar beneficial effects are expected when this gelled composition is applied for health foods.

What is claimed is:

1. A homogeneous gelled composition, comprising:
   a gelling agent; and
   an active ingredient that adsorbs material;
   wherein the gelled composition is made by heating an aqueous composition comprising the gelling agent and the active ingredient, and allowing the resulting mixture to form the homogeneous gelled composition.

2. The gelled composition of claim 1 where the active ingredient adsorbs material in the gastrointestinal tract.

3. The gelled composition of claim 2 where the composition is a topical composition.

4. The gelled composition of claim 1 where the active ingredient is an exchange resin.

5. The gelled composition of claim 1 where the active ingredient is an anion exchange resin, a cation exchange resin, or both.

6. The gelled composition of claim 1 where the active ingredient is activated carbon granules.

7. The gelled composition of claim 1 where the active ingredient is selected from the group consisting of biologically active salts of cholestyramine, biologically active salts of polystyrene sulfonate, and mixtures thereof.

8. The gelled composition of claim 1 where the gelling agent is selected from the group consisting of pectin, agar, arabic gum, xanthan gum, tragacanth gum, karaya gum, ghatti gum, guar gum, gellan gum, locust bean gum, alginic acid, a pharmaceutically acceptable alginate salt, carrageenan, gelatin, dextrin, starches, corn starch, rice starch, wheat starch, potato starch, pueraria starch, tapioca starch, carboxymethyl starch, hydroxypropyl starch, hydroxyethyl starch, chemically cross-linked starch, celluloses, hydroxypropylmethyl cellulose, carboxymethyl cellulose, methyl cellulose, methylethyl cellulose, hydroxypropyl cellulose, crystalline cellulose, polyvinyl alcohol, polyvinylpyrrolidone, polyethylene glycol, mannans, and combinations thereof.

9. The gelled composition of claim 1 where the active ingredient is selected from the group consisting of biologically active salts of cholestyramine, biologically active salts of polystyrene sulfonate, and mixtures thereof, and the gelling agent is selected from the group consisting of pectin, agar, arabic gum, xanthan gum, tragacanth gum, karaya gum, ghatti gum, guar gum, gellan gum, locust bean gum, alginic acid, a pharmaceutically acceptable alginate salt, carrageenan, gelatin, dextrin, starches, corn starch, rice starch, wheat starch, potato starch, pueraria starch, tapioca starch, carboxymethyl starch, hydroxypropyl starch, hydroxyethyl starch, chemically cross-linked starch, celluloses, hydroxypropylmethyl cellulose, carboxymethyl cellulose, methyl cellulose, methylethyl cellulose, hydroxypropyl cellulose, crystalline cellulose, polyvinyl alcohol, polyvinylpyrrolidone, polyethylene glycol, mannans, and combinations thereof.

10. The gelled composition of claim 1 where the gelling agent comprises pectin.

11. The gelled composition of claim 1 where the gelling agent comprises pectin and agar.

12. The gelled composition of claim 1 where the gelled composition comprises from about 0.01% to about 10% w/w gelling agent.

13. The gelled composition of claim 1 where the gelling agent comprises from about 0.5% to about 2.5% pectin.

14. The gelled composition of claim 1 where the gelling agent comprises from about 0.1% to about 0.5% agar.

15. The gelled composition of claim 1 where the gelling agent comprises from about 0.5% to about 2% gelatin.

16. The gelled composition of claim 1 where the gelled composition is a pharmaceutical composition.

17. The gelled composition of claim 1 where the gelled composition is a food.

18. A method for administering a material-adsorbing gelled composition to a subject, comprising:
heating an aqueous composition comprising a gelling agent and an active ingredient that adsorbs material;
allowing the resulting mixture to form a homogeneous gelled composition; and administering the homogeneous gelled composition to a subject.

19. The method according to claim 18 where the gelled composition is administered to the gastrointestinal tract.

20. The method according to claim 18 where the composition is a topical composition.

21. The method according to claim 18 where the active ingredient is an exchange resin.

22. The method according to claim 18 where the active ingredient is an anion exchange resin, a cation exchange resin, or both.

23. The method according to claim 18 where the active ingredient is activated carbon granules.

24. The method according to claim 18 where the active ingredient is selected from the group consisting of biologically active salts of cholestyramine, biologically active salts of polystyrene sulfonate, and mixtures thereof.

25. The method according to claim 18 where the gelling agent is selected from the group consisting of pectin, agar, arabic gum, xanthan gum, tragacanth gum, karaya gum, ghatti gum, guar gum, gellan gum, locust bean gum, alginic acid, a pharmaceutically acceptable alginate salt, carrageenan, gelatin, dextrin, starches, corn starch, rice starch, wheat starch, potato starch, pueraria starch, tapioca starch, carboxymethyl starch, hydroxypropyl starch, hydroxyethyl starch, chemically cross-linked starch, celluloses, hydroxypropylmethyl cellulose, carboxymethyl cellulose, methyl cellulose, methylethyl cellulose, hydroxypropyl cellulose, crystalline cellulose, polyvinyl alcohol, polyvinylpyrrolidone, polyethylene glycol, mannans, and combinations thereof.

26. The method according to claim 18 where the active ingredient is selected from the group consisting of biologically active salts of cholestyramine, biologically active salts of polystyrene sulfonate, and mixtures thereof, and the gelling agent is selected from the group consisting of pectin, agar, arabic gum, xanthan gum, tragacanth gum, karaya gum, ghatti gum, guar gum, gellan gum, locust bean gum, alginic acid, a pharmaceutically acceptable alginate salt, carrageenan, gelatin, dextrin, starches, corn starch, rice starch, wheat starch, potato starch, pueraria starch, tapioca starch, carboxymethyl starch, hydroxypropyl starch, hydroxyethyl starch, chemically cross-linked starch, celluloses, hydroxypropylmethyl cellulose, carboxymethyl cellulose, methyl cellulose, methylethyl cellulose, hydroxypropyl cellulose, crystalline cellulose, polyvinyl alcohol, polyvinylpyrrolidone, polyethylene glycol, mannans, and combinations thereof.

27. The method according to claim 18 where the gelling agent comprises pectin.

28. The method according to claim 18 where the gelling agent comprises pectin and agar.

29. The method according to claim 18 where the gelled composition comprises from about 0.01% to about 10% w/w gelling agent.

30. A method for making a homogeneous gelled composition, comprising:
providing a gelling agent and an active ingredient;
forming an aqueous composition comprising the gelling agent and the active ingredient;
heating the aqueous composition; and
allowing the mixture to form a homogeneous gel.

31. The method according to claim 30 where the mixture is heated to a temperature of from about 50° C. to about 100° C.

32. The method according to claim 30 where the mixture is heated to a temperature of from about 70° C. to about 90° C.

33. The method according to claim 30 where the active ingredient adsorbs material in the gastrointestinal tract.

34. The method according to claim 30 where the composition is a topical composition.

35. The method according to claim 30 where the active ingredient is an exchange resin.

36. The method according to claim 30 where the active ingredient is an anion exchange resin, a cation exchange resin, or both.

37. The method according to claim 30 where the active ingredient is activated carbon granules.

38. The method according to claim 30 where the active ingredient is selected from the group consisting of biologically active salts of cholestyramine, biologically active salts of polystyrene sulfonate, and mixtures thereof.

39. The method according to claim 30 where the gelling agent is selected from the group consisting of pectin, agar, arabic gum, xanthan gum, tragacanth gum, karaya gum, ghatti gum, guar gum, gellan gum, locust bean gum, alginic acid, a pharmaceutically acceptable alginate salt, carrageenan, gelatin, dextrin, starches, corn starch, rice starch, wheat starch, potato starch, pueraria starch, tapioca starch, carboxymethyl starch, hydroxypropyl starch, hydroxyethyl starch, chemically cross-linked starch, celluloses, hydroxypropylmethyl cellulose, carboxymethyl cellulose, methyl cellulose, methylethyl cellulose, hydroxypropyl cellulose, crystalline cellulose, polyvinyl alcohol, polyvinylpyrrolidone, polyethylene glycol, mannans, and combinations thereof.

40. The method according to claim 30 where the active ingredient is selected from the group consisting of biologically active salts of cholestyramine, biologically active salts of polystyrene sulfonate, and mixtures thereof, and the gelling agent is selected from the group consisting of pectin, agar, arabic gum, xanthan gum, tragacanth gum, karaya gum, ghatti gum, guar gum, gellan gum, locust bean gum, alginic acid, a pharmaceutically acceptable alginate salt, carrageenan, gelatin, dextrin, starches, corn starch, rice starch, wheat starch, potato starch, pueraria starch, tapioca starch, carboxymethyl starch, hydroxypropyl starch, hydroxyethyl starch, chemically cross-linked starch, celluloses, hydroxypropylmethyl cellulose, carboxymethyl cellulose, methyl cellulose, methylethyl cellulose, hydroxypropyl cellulose, crystalline cellulose, polyvinyl alcohol, polyvinylpyrrolidone, polyethylene glycol, mannans, and combinations thereof.

41. The method according to claim 30 where the gelling agent comprises pectin.

42. The method according to claim 30 where the gelling agent comprises pectin and agar.

43. The method according to claim 30 where the gelled composition comprises from about 0.01% to about 10% w/w gelling agent.

44. A homogeneous gelled composition, comprising:
   a gelling agent; and
   an active ingredient selected from activated carbon granules and biologically active salts of polystyrene sulfonate.

45. A homogeneous gelled composition, comprising:
   a gelling agent comprising pectin and agar; and
   an active ingredient that adsorbs material.

46. A homogeneous gelled composition, comprising:
   a gelling agent; and
   about 5.0 to about 20.0 weight percent cholestyramine as an active ingredient that adsorbs material, based on the total weight of the composition.

47. A method for administering a material-adsorbing gelled composition to a subject, comprising:
   providing a homogeneous gelled composition comprising a gelling agent and an active ingredient selected from activated carbon granules and biologically active salts of polystyrene sulfonate; and
   administering the homogeneous gelled composition to a subject.

48. A method for administering a material-adsorbing gelled composition to a subject, comprising:
   providing a homogeneous gelled composition comprising an active ingredient that adsorbs material and a gelling agent comprising pectin and agar; and
   administering the homogeneous gelled composition to a subject.

49. A method for administering a material-adsorbing gelled composition to a subject, comprising:
   providing a homogeneous gelled composition comprising a gelling agent and about 5.0 to about 20.0 weight percent cholestyramine as an active ingredient that adsorbs material, based on the total weight of the composition; and
   administering the homogeneous gelled composition to a subject.

50. A method for making a homogeneous gelled composition, comprising:
   forming an aqueous composition comprising a gelling agent;
   heating the aqueous composition;
   adding an active ingredient to the heated aqueous composition; and
   allowing the resulting mixture to form a homogeneous gel.

51. The method according to claim 50, wherein the resulting mixture cools to form the gel.

52. The method according to claim 50, wherein the active ingredient is selected from biologically active salts of cholestyramine, biologically active salts of polystyrene sulfonate, and mixtures thereof.

* * * * *